(12) United States Patent
Gabbay

(10) Patent No.: US 6,679,914 B1
(45) Date of Patent: Jan. 20, 2004

(54) IMPLANTABLE ORTHOPEDIC SUPPORT APPARATUS

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/712,100

(22) Filed: Nov. 14, 2000

(51) Int. Cl.[7] .................................................. A61F 2/06
(52) U.S. Cl. .................................. 623/14.12; 623/11.11
(58) Field of Search ........................... 623/11.11, 13.11, 623/14.12, 23.72, 23.73, 23.74, 23.75, 23.76

(56) References Cited

U.S. PATENT DOCUMENTS

| | | | |
|---|---|---|---|
| 3,867,728 A | * 2/1975 | Stubstad et al. ..... | 128/DIG. 21 |
| 4,599,084 A | * 7/1986 | Nashef ........................ | 128/898 |
| 4,919,667 A | * 4/1990 | Richmond ............... | 623/14.12 |
| 5,618,312 A | 4/1997 | Yui et al. | |
| 5,733,337 A | * 3/1998 | Carr et al. ................. | 435/325 |
| 5,824,094 A | 10/1998 | Serhan et al. .................. | 623/17 |
| 5,855,620 A | 1/1999 | Bishopric et al. | |
| 5,888,222 A | 3/1999 | Coates et al. .................. | 623/17 |
| 5,968,096 A | * 10/1999 | Whitson et al. ............. | 424/422 |
| 6,039,763 A | 3/2000 | Shelokov ...................... | 623/17 |
| 6,046,379 A | 4/2000 | Stone et al. .................. | 623/11 |
| 6,093,204 A | 7/2000 | Stone ....................... | 623/14.12 |

OTHER PUBLICATIONS

International Search Report.
"Nitinol Solutions", Product brochure of Raychem Corporation, Electronics OEM Components Division, Menlo Park, California, Copyright date of 1999.

* cited by examiner

Primary Examiner—David J. Isabella
(74) Attorney, Agent, or Firm—Tarolli, Sundheim, Covell & Tummino L.L.P.

(57) ABSTRACT

An implantable support apparatus cushions between articulating structures, such as bone or other tissue. The apparatus includes a plurality of sheets of a substantially biocompatible tissue, which are connected together to form a laminated stack of the biocompatible tissue. Alternatively, the prosthesis may be formed of a molded protein, which has been cross-linked and substantially detoxified.

20 Claims, 4 Drawing Sheets

IMPLANTABLE ORTHOPEDIC SUPPORT APPARATUS

TECHNICAL FIELD

The present invention relates to implantable devices and, more particularly to an implantable orthopedic support and a method for making the support.

BACKGROUND

Various joints in animals, such as humans, are defined by a fibrocartilaginous disc interposed between articulating bony surfaces. Joints may be classified according to the amount of movement they permit. Moveable joints may permit relative movement between the adjoining bones in several ways: gliding, angular, circumduction, and/or rotation. Joints, because of their location and constant use, are prone to stress, which may result in injuries. A common injury occurs to the fibrocartilaginous disc interconnecting two articulating bony surfaces. The fibrocartilaginous disc also may degenerate over time. By way of illustration, two fibrocartilage discs of particular interest include intervertebral discs and menisci of knee joints.

A human intervertebral disc is located between the endplates of adjacent vertebrae to stabilize the spine, distribute forces between vertebrae and cushion vertebral bodies. The intervertebral disc employs various modes of articulation that provide for changing the instant center of rotation of adjacent vertebral surfaces relative to one another and permit lateral-to-lateral and anteroposterior translation of vertebrae relative to one another.

Spinal discs may be displaced or damaged due to trauma, disease or aging. One common condition, which is referred to as a herniated or ruptured disc, occurs when the annulus fibrous allows the nucleus pulposus to protrude into the vertebral canal. The protruding nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced, which may lead to instability of the spine, pain and decreased mobility.

Sometimes the only relief from the symptoms of these conditions is discectomy, or surgical removal of a portion or all of an intervertebral disc followed by fusion of the adjacent vertebrae. When a disc is removed, a space is formed, which if left untreated, may allow the disc space to collapse. In addition to severe pain, a collapse of the disc space may cause instability of the spine, abnormal joint mechanics, premature development of arthritis and/or nerve damage.

An undamaged meniscus of a knee joint provides shock absorption for the knee by ensuring proper force distribution, stabilization, and lubrication for the interacting bone surfaces within the knee joint. Much of the shock absorbing function of the medial and lateral menisci is derived from the elastic properties inherent to cartilage. When a meniscus is damaged, such as through injury, disease, or inflammation, arthritic changes occur in the knee joint, which may result in a loss of function and/or pain.

Since joint cartilage in adults does not naturally regenerate to a significant degree once it is destroyed, damaged adult menisci have historically been treated by a variety of surgical interventions including removal and replacement with prosthetic devices. In one respect, a meniscus prosthesis may be utilized. Examples of meniscus prostheses may be formed of resilient materials, such as silicone rubber or natural rubber, collagen, tendon, or fibrocartilage. By way of further illustration, a meniscus heterograft has been proposed to replace a damaged human meniscus.

SUMMARY

The present invention relates to an implantable support apparatus for cushioning between articulating structures, such as bone or other tissue. The apparatus includes a plurality of sheets of a substantially biocompatible tissue, which are connected together to form a laminated stack of the tissue. In accordance with one particular aspect, each sheet in the stack is treated animal pericardium.

The shape of the laminated stack is determined from the shape and configuration of each of the plurality of sheets that comprise the stack. The stack may be dimensioned and configured according to the particular use in which it is to be employed. For example, the stack may be kidney shaped, circular, annular, or other shapes and may include one ore more apertures extending through the stack to help provide a desired level of cushioning.

One aspect of the present invention provides an implantable orthopedic support apparatus. The apparatus includes a plurality of generally flat sheets of a flexible tissue material. The plurality of sheets are connected together so as to inhibit movement between adjacent sheets.

According to one particular aspect, each of the sheets may be dimensioned and configured according to the dimensions and configuration of human vertebrae, such that the apparatus provides an intervertebral disc prosthesis. According to another aspect, one or more apertures may extend through the plurality of sheets and the apparatus may be dimensioned, such that it may be utilized to replace a meniscus (or menisci) of a knee joint.

Yet another aspect provides an implantable orthopedic support apparatus. The apparatus includes a molded and cross-linked protein structure having a pair of surfaces for engaging a respective articulating structure when implanted. The molded and cross-linked protein structure is detoxified to mitigate calcification.

Another aspect of the present invention provides a method of manufacturing an implantable orthopedic support apparatus. The method includes forming a plurality of similarly dimensioned and configured sheets from a flexible biocompatible material and axially aligning the plurality of sheets to form a stack of the plurality of sheets. The stack of sheets is secured together so as to mitigate shearing between adjacent sheets.

Still another aspect of the present invention provides a method of manufacturing an implantable orthopedic support apparatus. The method includes molding a protein material into a desired shape having a opposed sides dimensioned and configured for engaging respective articulating structures of a patient. The molded protein material is cross-linked and substantially detoxified to form the implantable orthopedic support apparatus. As a result, after the support apparatus is implanted, the support apparatus provides shock-absorbing properties between respective articulating structures of the patient and mitigates calcification of the implanted prosthesis.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which.

DESCRIPTION OF THE INVENTION

The present invention provides a disc prosthesis to cushion between articulating structures, such as bone or other tissue. The prosthesis includes a plurality of sheets of a substantially biocompatible tissue, which have been connected together to form a laminated stack of tissue. The application of a stack according to the present invention is determined by the dimensions and configuration of each of the plurality of sheets that comprise the stack. While the following description illustrates certain types of prostheses, including an intervertebral disc and a meniscus, those skilled in the art will understand and appreciate other types of implantable prostheses may be implemented in accordance with the present invention.

Figure 1:
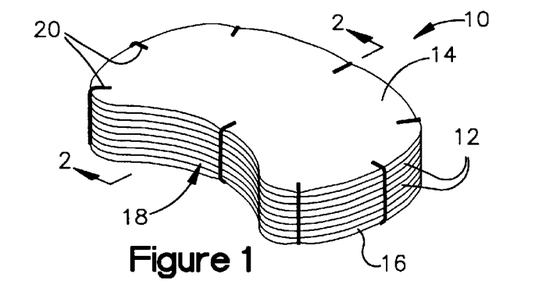
FIG. 1 is an isometric view of a disc prosthesis in accordance with the present invention.
Figure 2:
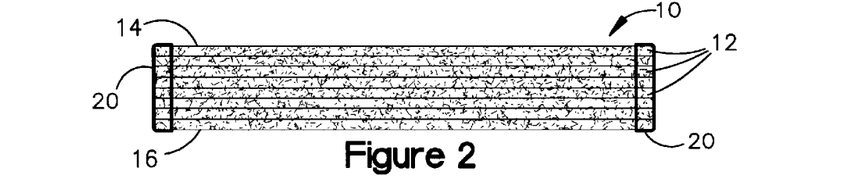
FIG. 2 is a cross-sectional view taken along line 2—2 of FIG. 1.

Turning now to FIGS. 1 and 2, a multi-layered tissue prosthesis 10 in accordance with an aspect of the present invention is illustrated. The prosthesis 10 includes a plurality of sheets 12 of a substantially elastic, biocompatible tissue material. The sheets 12 are sandwiched together in a superimposing relationship between a pair of axially spaced apart end sheets 14 and 16. Each sheet may be cut from one or more elongated sheets of suitable tissue so as to have a desired configuration and dimensions, which may be substantially similar. The sheets are then stacked in a desired axial arrangement, such that their side edges are substantially axially aligned.

In this particular example, the prosthesis 10 has a generally kidney-shaped axial cross section, with part of its sidewall being indented, indicated at 18, to provide a shape corresponding to the shape of a vertebral body of a human vertebra. Advantageously, the dimensions and configuration of the prosthesis 10 can be easily customized according to the particular dimensions and configurations needed for a patient. Such customization may be performed by the manufacturer or the surgeon just prior to implantation.

With the sheets 12 arranged in a desired configuration, the sheets are connected together to form the prosthesis 10 in accordance with an aspect of the present invention. The sheets 12 may be sewn together by nonadsorbable sutures 20 applied axially through a perimeter portion of all the sheets that form the prosthesis 10. Suture holes (not shown) may be formed through each sheet 12 near a perimeter thereof to facilitate sewing the sheets together. By way of example, an electromechanical sewing machine may be utilized to sew axially through the perimeter portion of the sheets 12. Additionally or alternatively, a suitable surgical adhesive may be applied between adjacent layers to bond adjacent sheets together. As a result of the sutures 20 and/or adhesive, shearing between adjacent sheets 12 is mitigated when the prosthesis 10 is subject to stress.

In accordance with an aspect of the present invention, the sheets 12 are formed of animal pericardium (e.g., bovine, equine, porcine, etc.). Typically a sheet of pericardium has a thickness of about 0.7 mm. The number of sheets 12 used in a prosthesis 10 thus will vary according to a desired thickness of the prosthesis, which may range from about 3 mm to about 1 cm or more. By way of example, the tissue may be treated by immersing it in a suitable glutaraldehyde solution for a time period of about twenty-four hours. The tissue may be trimmed to a configuration before or after the tissue treatment process. Such tissue treatment processes are well known with respect to heart valves and other natural tissue prostheses.

By way of further illustration, the natural tissue sheets 12 may be cross-linked with an aldehyde solution (e.g., glutaraldehyde) and undergo a detoxification process, which may include heparin bonding. In particular, the individual sheets may be formed from sheets of a NO-REACT® tissue product, such as elongated pericardial patches, which are commercially available from Shelhigh, Inc., of Millburn, N.J. Those skilled in the art will thus understand and appreciate that individual sheets of NO-REACT® tissue (or other sheets of biocompatible, generally elastic material) may be assembled to form a disc prosthesis in accordance with the teachings contained herein.

The NO-REACT® tissue helps improve the biocompatibility of the resulting prosthesis, thereby mitigating the likelihood of a patient rejecting the implanted prosthesis 10. Animal pericardium, when treated in this manner, also becomes substantially elastic and resilient as well as resist calcification. As a result, a prosthesis formed of a stack of such sheets to form a prosthesis, in accordance with an aspect of the present invention, exhibits desirable shock-absorbing properties similar to natural intervertebral discs and other fibrocartilaginous tissue. The amount of elasticity and resilience is proportional to the combined elasticity and resilience of the individual sheets that form the prosthesis 10.

It is to be understood and appreciated by those skilled in the art that other types of treated tissue (e.g., natural or synthetic) may be utilized to form a prosthesis 10 in accordance with the present invention.

The prosthesis 10 may be stored in a dry or wet condition. For example, it may be desirable to dry the prosthesis 10 (partially or completely) prior to storing the prosthesis. By storing the prosthesis 10 in a dry condition, for example, the prosthesis becomes stiffer and, in turn, facilitates implantation of the prosthesis. Once implanted, the dry prosthesis 10 will absorb fluid or hydrate from surrounding fluids in the body and return to its desired flexible and resilient condition. Fluids also may be applied to help hydrate the prosthesis 10 to a desired condition.

Figure 2A:
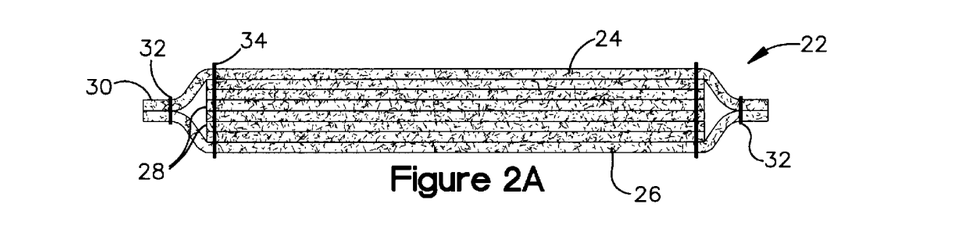
FIG. 2A is a cross-sectional view of disk prosthesis in accordance with another aspect of the present invention.

FIG. 2A illustrates a cross-sectional view of a prosthesis 22 in accordance with another aspect of the present invention. In order to facilitate implantation, axially opposed end sheets 24 and 26 of the prosthesis 22 are dimensioned and configured to be larger than the intermediate sheets 28. The outer sheets 24 and 26 may be positioned relative to the other sheets 28 so that a peripheral edge of the end sheets extends radially outwardly relative to the side edge of the intermediate sheets 28. The peripheral edge from the outer sheets 24 and 26 form a flange 30 that may be secured to an adjacent ligament or other connective tissue to help secure the prosthesis 22 at a desired position when implanted. The peripheral edges further may be connected together by sutures 32 and/or a suitable surgical adhesive, as described above. Additional sutures 34 further can be applied through all the sheets 24, 26 and 28 to mitigate shearing between adjacent sheets and, in turn, maintain a desired shape for the prosthesis 22.

Figure 3:
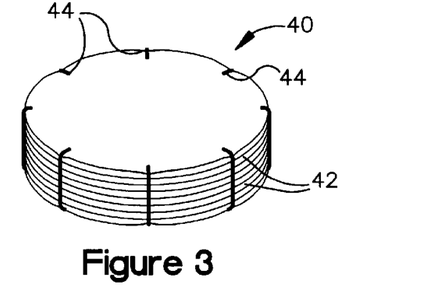
FIG. 3 is an isometric view of another disc prosthesis in accordance with the present invention.

FIG. 3 illustrates another example of a prosthesis 40 having a substantially circular cross-section. In this example, the prosthesis 40 is formed of a plurality of generally circular sheets 42 having a similar configuration, which have been axially aligned to form a stack of circular sheets. The sheets 42 are connected together, such as by sutures 44 and/or a surgical adhesive. The individual sheets further may include suture holes formed through each sheet near a perimeter edge thereof. The sutures 44 and/or a surgical adhesive can be used to connect the sheets together to form the prosthesis 30 having the desired shape and thickness. The sheets 42, for example, are formed of an animal pericardial tissue, such as described above.

Figure 4:
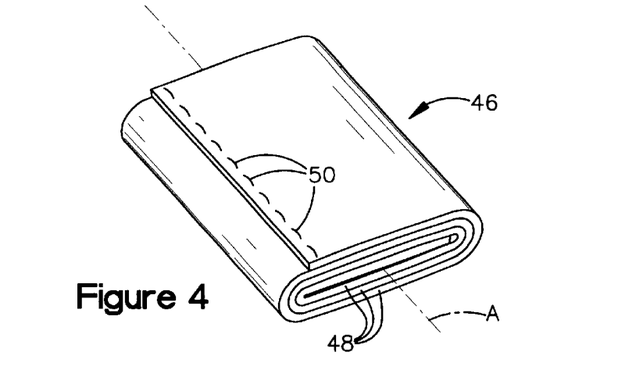
FIG. 4 is an isometric view of yet another disc prosthesis in accordance with the present invention.

FIG. 4 illustrates another example of an implantable orthopedic support prosthesis 46 in accordance with an aspect of the present invention. The prosthesis is formed from one or more elongated sheets of a suitable biocompatible material. The sheet has been folded (e.g., rolled) on itself multiple times about an axis A, which is transverse to a long axis of the sheet of material. The prosthesis 46 thus includes a plurality of overlapping layers 48 of the tissue material. The layers may be sewn together via sutures 50 to maintain a desired shape for the prosthesis 46. Each successive layer 48 is spaced radially from the axis A an increased distance.

It will be appreciated that the diameter of the prosthesis 46 may be dimensioned and configured according to where it is intended to be implanted and further may be customized for a given patient. For example, the cross sectional diameter of the prosthesis 46 (e.g., perpendicular to the axis A) may be adjusted, such as by removing one or more outer layers of the tissue material. Such adjustments can be made by the manufacturer or by the surgeon prior to implantation. That is, the sutures 50 may be removed and any portion of one or more layers 48 may be removed from the prosthesis 46 to provide a desired size. One the desired size exists, sutures may be applied through the prosthesis 46 to help maintain the prosthesis in the appropriate configuration and mitigate movement between the respective layers. It is also to be appreciated that a suitable surgical adhesive could be utilized to help hold the adjacent layers 48 of the prosthesis 46 together.

The prosthesis 46 may be formed of a natural tissue material that has been cross-linked with an aldehyde solution (e.g., glutaraldehyde) and has undergone a detoxification process, such as described above. By way of further illustration, the sheet may be a NO-REACT® tissue product, such as elongated pericardial patch, which has been folded into a desired shape, such as shown in FIG. 4. Those skilled in the art will thus understand and appreciate that other shapes could be formed by rolling or folding one or more sheets of a suitable biocompatible material. The resulting prosthesis 46 thus provides an elastic disc prosthesis operative to absorb shock due to forces applied transverse relative to the overlapping layers 48.

Figure 5:
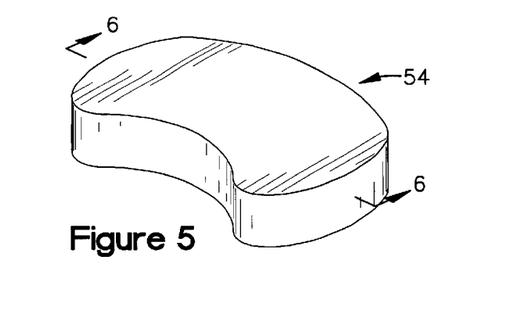
FIG. 5 is an isometric view of yet another prosthesis in accordance with the present invention.
Figure 6:
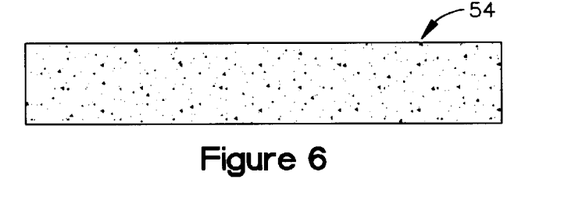
FIG. 6 is a side sectional view taken along line 6—6 of FIG. 5.

FIGS. 5 and 6 illustrate another example of an implantable prosthesis 54, in accordance with an aspect of the present invention, such as may be used to replace an intervertebral disc. In this example, the prosthesis 54 is formed of a protein material that has been cross-linked, such as with glutaraldehyde, into a desired kidney shape. It is to be appreciated that the prosthesis could be molded into other shapes, such as described below.

The protein may be animal plasma, collagen, fibrinogen, etc. After the cross-linked protein has a desired texture (e.g., generally resilient and elastic) and shape, it is detoxified, such as according to a NO-REACT® detoxification treatment process. The resulting prosthesis 54 further may be covered with a sheet of natural tissue material, such as animal pericardium, which also has been cross-linked and detoxified. For example, the sheet may be NO-REACT pericardial patch, which is commercially available from Shelhigh, Inc. of Millburn, N.J. The combination of cross-linking and detoxification provides a nonabsorbable elastic prosthesis capable of providing a desired shock absorbing function when inserted between articulating structures. Additionally, such treatment mitigates calcification as well as the likelihood of a patient rejecting the implant.

Figure 7:
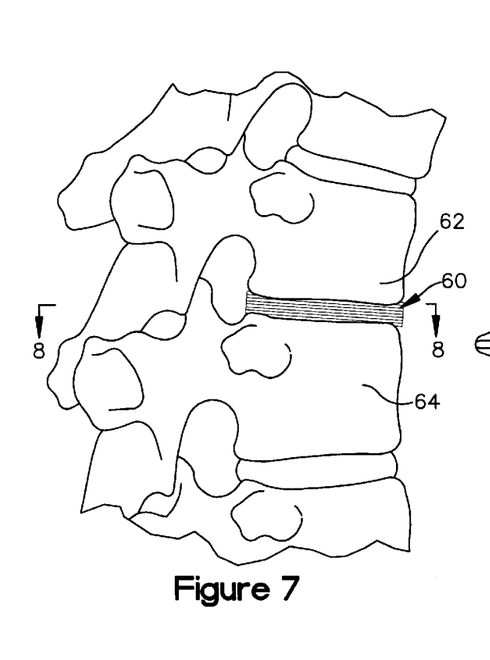
FIG. 7 is an example of a disc prosthesis, in accordance with the present invention, implanted as an intervertebral disc.
Figure 8:
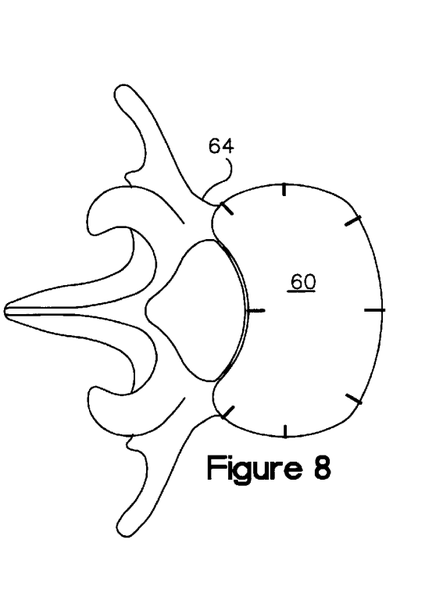
FIG. 8 is a side sectional view taken along line 8—8 of FIG. 7.

FIGS. 7 and 8 illustrate a disc prosthesis 60, in accordance with an aspect of the present invention, employed to replace a damaged or degenerated intervertebral disc. For example, the disc prosthesis 60 may be utilized to prevent the collapse of the space left after discectomy. The disc prosthesis 60 is positioned between adjacent upper and lower vertebrae 62 and 64, respectively. As illustrated in FIG. 8, the prosthesis 60 is dimensioned and configured (e.g., kidney-shaped) according to the dimensions and configuration of the vertebral bodies of the adjacent vertebrae 62 and 64. In order to maintain a desired position of the disc 60, the disc may be sutured to surrounding tissue, such as a ligament or other connective tissue. As mentioned above with respect to FIG. 2A, the prosthesis 60 also could include a flange to facilitate attachment to surrounding tissue.

Figure 9:
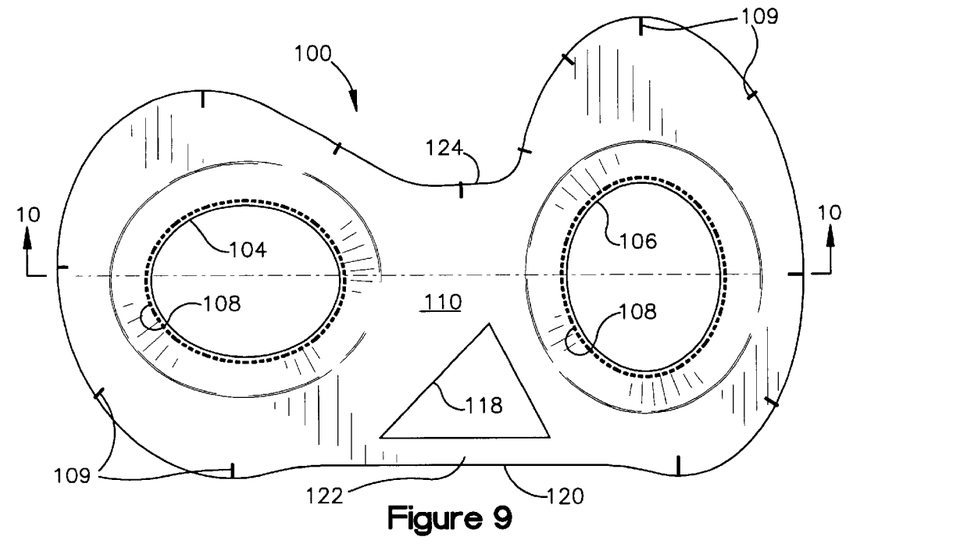
FIG. 9 is an example of another disc prosthesis in accordance with the present invention.
Figure 10:
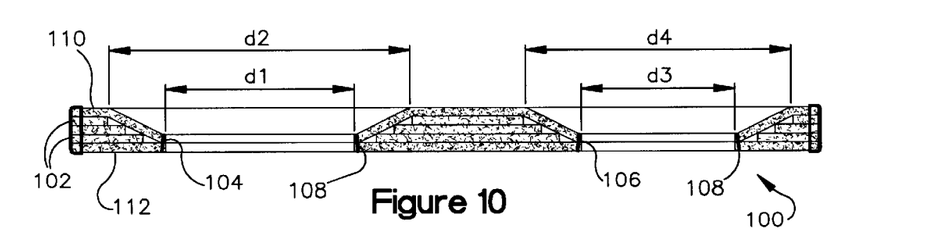
FIG. 10 is a side sectional view taken along line 10—10 of the prosthesis of FIG. 9.

FIGS. 9 and 10 illustrate another implantable support prosthesis 100 in accordance with an aspect of the present invention. The prosthesis 100 is formed a plurality of layers 102 of a biocompatible tissue material that have been aligned and connected together to form the resulting prosthesis.

For example, each layer is formed from a sheet 102 of a tissue material, such as animal pericardium, that has been treated to render it substantially biocompatible. As mentioned above, the sheets 102 may be cross-linked with glutaraldehyde and undergo a detoxification process with heparin bonding. In particular, the individual layers of tissue may be formed from one or more sheets of a NO-REACT® tissue product, which are commercially available from Shelhigh, Inc. of Millburn, N.J. Those skilled in the art will understand and appreciate that other types of biocompatible tissue material (e.g., natural or synthetic) also could be utilized in accordance with the present invention.

In the example of FIG. 9, first and second apertures 104 and 106 extend axially through the prosthesis 100. For example, the first aperture 104 is dimensioned and configured for cushioning between a lateral condyle and corresponding articulating surface of a tibia. Similarly, the other aperture 106 is dimensioned and configured for cushioning between a medial condyle and a corresponding articulating surface of a tibia.

In accordance with an aspect of the present invention, the cross-sectional thickness of the prosthesis 100 tapers to a reduced thickness at each aperture 104, 106, as shown in the cross-sectional view of FIG. 10. In this example, each aperture formed through each intermediate sheet of the prosthesis 100 at apertures 104 and 106 may have varying diameters. As a result, the thickness of the prosthesis 100 near the apertures 104 and 106 tapers to a reduced thickness as compared to the thickness away from such apertures, thereby providing generally frusto-conical apertures 104 and 106 through the prosthesis 100. Sutures 108 are applied axially through the prosthesis 100 surrounding the apertures 104 and 106. Sutures 109 also are applied axially through the prosthesis 100 near a periphery of the prosthesis.

By way of further illustration, the apertures 104 formed through axially opposed end sheets 110 and 112 have diameters that are substantially the same size. Similarly, the apertures 106 formed through the sheets 110 and 112 are substantially the same size. The end sheets 110 and 112 thus are able to enclose the intermediate sheets, as shown in FIGS. 9 and 10. The corresponding apertures 104 and 106 formed through at least some of the intermediate sheets have diameters d2 and d4 which are greater than the respective diameters d1 and d3 of the axially opposed sheets 110 and 112. In this way, a desired tapering is provided around each aperture 104 and 106, which may conform to the contour of articulating structures (e.g., a femur and tibia), which the prosthesis 100 is designed to cushion.

It will be understood and appreciated that a desired taper may be formed by other techniques or orientations of the associated layers 102. For example, the intermediate sheets could be configured to have other amounts of tapering or no tapering depending upon the intended implantation site.

The prosthesis 100 includes another aperture 118 near one of its side edges 120. A bridge 122 of tissue interconnects parts of the prosthesis on opposed sides of the aperture 118. In the example of FIG. 9, the aperture 118 is triangular, although other shapes could be used. The bridge 122, which may be formed of one or more layers of the tissue material (e.g., the axially opposed end sheets 110 and 112), is operative to perform a function similar to a transverse ligament when the prosthesis 100 is implanted. A recess 124 defines an indented sidewall portion of the prosthesis 100. The aperture 118 and the recess 124 are configured to correspond to the contour of the cruciate ligaments of the knee. As a result, the prosthesis is able to provide a desired elastic support and cushion between a femur and tibia while not interfering with other associate anatomical support structures.

Figures 11, 12, 13:
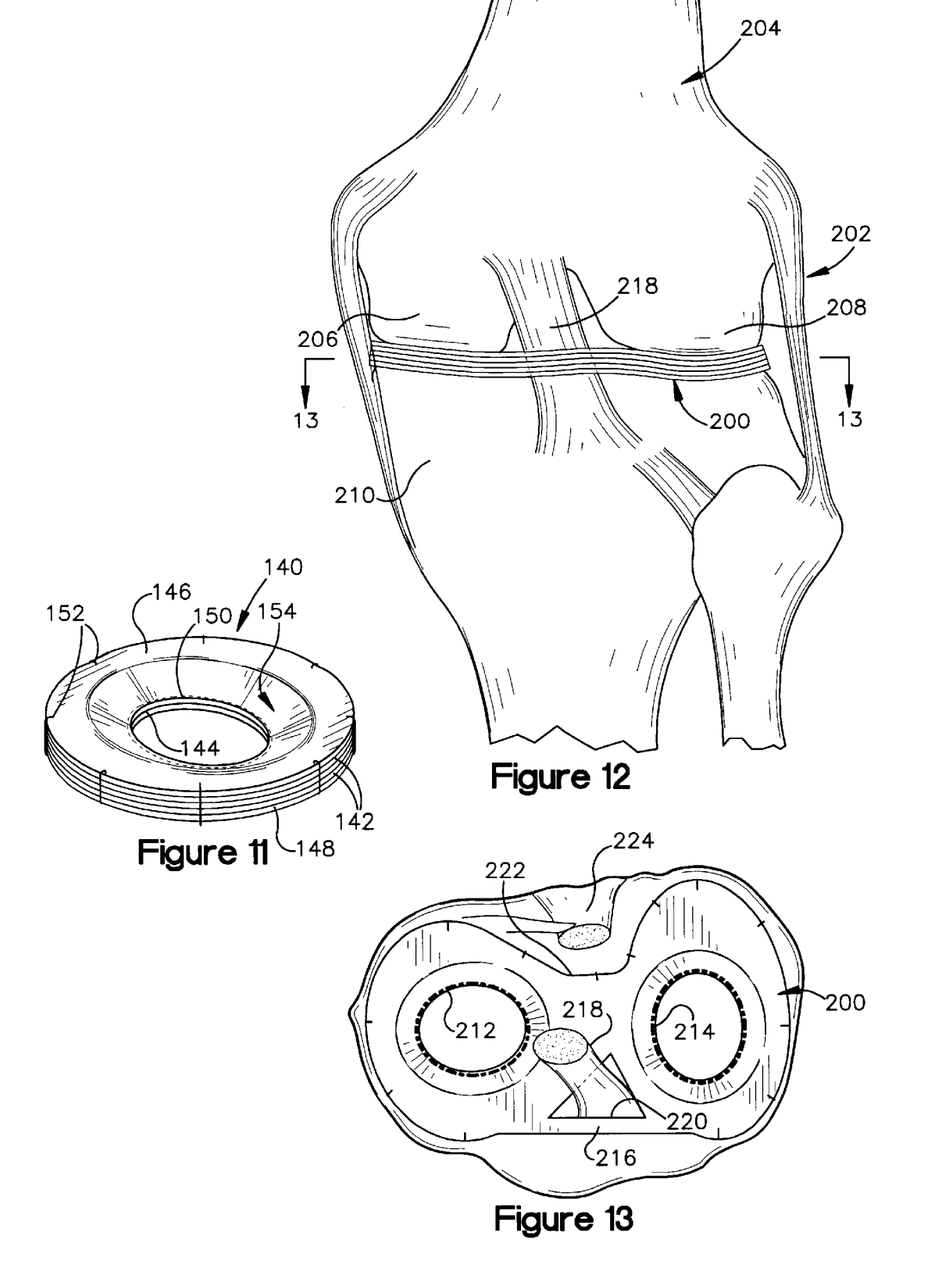
FIG. 11 is an example of another disc prosthesis in accordance with the present invention.
FIG. 12 is an example of a mensical prosthesis implanted at a knee joint in accordance with the present invention.
FIG. 13 is a side sectional view taken along line 13—13 of FIG. 12.

FIG. 11 illustrates another example of a meniscus prosthesis 140 in accordance with an aspect of the present invention. The meniscus prosthesis 140 has a substantially annular cross-section and is formed of a plurality of substantially coaxial layers 142 of a biocompatible tissue material. In particular, the prosthesis 140 has a central aperture 144 extending through the layers 142. Each layer 142 has a similar outer diameter and is generally axially aligned and connected together, such as by sutures and/or a suitable adhesive. For example, axially opposed end layers 146 and 148 of the prosthesis 140 enclose one or more intermediate layers of material. Sutures 150 are applied near the inner diameter of the end layers 146 and 148 and additional sutures 152 are applied near an outer periphery thereof.

As mentioned above in the example of FIGS. 9 and 10, the inner diameter of the component layers 142 may be dimensioned and configured so that the thickness of the prosthesis 140 near the aperture 144 tapers radially inwardly to a reduced thickness, which tapered portion is indicated at 154. For example, the axial thickness of the prosthesis 140 at its inner diameter may be defined by the axial thickness of the two outer layers or the two outer layers 146 and 148. It is to be appreciated that one or more of the intervening layers also could be dimensioned to have an inner diameter so as to be sandwiched between the outer layers 146 and 148.

The individual sheets 142, for example, are formed of animal pericardial tissue, such as described hereinabove. It is to be appreciated that other tissue materials (e.g., natural or synthetic) also could be used in accordance with the present invention.

FIGS. 12 and 13 illustrates a meniscal prosthesis 200 implanted at a knee joint 202 in accordance with an aspect of the present invention. The knee joint 202 includes femur 204 having a lateral condyle 206 and a medial condyle 208. The prosthesis 200 is interposed between articulating surfaces of a tibia 210 and the condyles 206 and 208. The prosthesis 200 helps cushion between the articulating surfaces of the condyles 206 and 208 and the tibia 210, such as during relative movement and/or stress between such surfaces.

When implanting the prosthesis 200, it may be necessary to first cut the bridge 216 so that the anterior cruciate ligament 218 may pass through a triangular aperture 220 formed through the prosthesis. The bridge 216 may be resecured to the prosthesis 200 (e.g., by sutures and/or adhesive) and, in turn, provide a stabilizing function similar to the transverse ligament. An opposed side of the prosthesis 200 has a recessed portion 222, which is dimensioned and configured so as to not interfere with the posterior cruciate ligament 224.

In view of the foregoing, the prosthesis 200 provides an elastic and resilient support that exhibits desirable shock-absorbing properties and biocompatibility. The amount of elasticity and resilience is proportional to the combined elasticity and resilience of the individual sheets that form the prosthesis 200.

Figure 14:
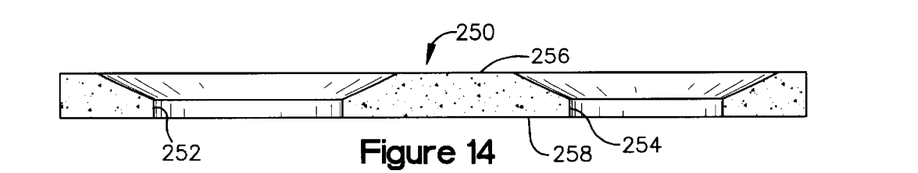
FIG. 14 is a cross-sectional view of another meniscal prosthesis in accordance with the present invention.

FIG. 14 illustrates another example of a meniscal prosthesis 250 in accordance with an aspect of the present invention. In this example, the prosthesis is formed of a molded protein that has been cross-linked with a suitable aldehyde solution (e.g., glutaraldehyde) into a desired configuration. As mentioned above, the protein may be animal blood plasma, collagen, fibrinogen, etc. After the cross-linked protein has a desired texture (e.g., generally resilient and elastic) and shape, it is detoxified, such as according to a NO-REACT® detoxification treatment process. The resulting prosthesis 250 is a resilient elastic composite structure that provides desired shock-absorbing properties. In addition, the detoxification and cross-linking provide a nonabsorbable prosthesis 250 that mitigates calcification as well as the likelihood of rejection after being implanted in a human patient.

The illustrated configuration is substantially identical to that shown and described with respect to FIG. 9 (except for the multiple layers in FIG. 9) and, therefore, a detailed description of its configuration has been omitted for purposes of brevity. Briefly stated, the prosthesis 250 includes a pair of apertures 252 and 254 extending axially through the prosthesis according to the location of a medial and lateral menisci of a patient. The diameter of each aperture at one side 256 of the prosthesis 250 is greater than the diameter of the aperture at the other side 258 of the prosthesis.

Figure 15:
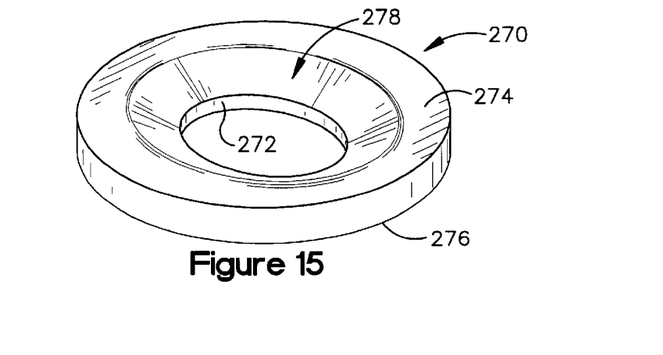
FIG. 15 is an example of another disc prosthesis in accordance with an aspect of the present invention.

FIG. 15 is another example of a meniscal prosthesis 270 having a configuration similar to the example of FIG. 11. However, in this example, the prosthesis 270 is formed from a molded protein structure that has been cross-linked and detoxified as described herein. In particular, the prosthesis 270 is molded to include an aperture 272 extending between opposed sides 274 and 276 of the prosthesis. The diameter of the aperture 272 at the side 274 is greater than the diameter of the aperture at its opposed side 276, as shown in FIG. 15. That is, the prosthesis 270 has a generally frusto-conical portion 278 interconnecting the opposed sides 274 and 276.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. An implantable orthopedic support apparatus, comprising:
   a plurality of generally flat sheets of a flexible tissue material comprising animal pericardium, the plurality of sheets being superimposedly connected together so as to inhibit movement between adjacent sheets, wherein the animal pericardium has been treated with an aldehyde solution and substantially detoxified.

2. The apparatus of claim 1, wherein the plurality of sheets includes at least three similarly dimensioned and configured sheets of the flexible tissue material arranged in an axial stack of the plurality of sheets.

3. The apparatus of claim 2, wherein at least a substantial portion of the at least three sheets have a kidney-shaped cross section to substantially conform to a cross-sectional contour of a vertebral body of human vertebrae, whereby the apparatus forms an intervertebral prosthesis.

4. The apparatus of claim 2, wherein at least a substantial portion of the plurality of sheets have a generally circular cross section.

5. The apparatus of claim 1, wherein the plurality of sheets define separate layers of at least one elongated sheet which has been folded on itself multiple time transverse to a long axis thereof.

6. An implantable orthopedic support apparatus, comprising:
   a plurality of generally flat sheets of a flexible tissue material, the plurality of sheets being superimposedly connected together so as to inhibit movement between adjacent sheets, the plurality of sheets including at least three similarly dimensioned and configured sheets of the flexible tissue material arranged in a substantially coaxial stack of the plurality of sheets, at least a substantial portion of the plurality of sheets have a generally circular cross section with a central aperture extending substantially coaxially through at least some of the plurality of sheets.

7. The apparatus of claim 6, the flexible tissue material having been treated with an aldehyde solution.

8. The apparatus of claim 7, the flexible tissue material further comprising animal pericardium.

9. An implantable orthopedic support apparatus, comprising:
   a plurality of generally flat sheets of a flexible tissue material, the plurality of sheets being superimposedly connected together so as to inhibit movement between adjacent sheets, wherein first and second apertures extend substantially coaxially through at least a substantial portion of the plurality of sheets, the first and second apertures being spaced apart from each other at locations according to locations of a patient's lateral and medial menisci, whereby the apparatus forms a meniscal prosthesis.

10. The apparatus of claim 9, wherein the first and second apertures extend axially through all the plurality of sheets.

11. The apparatus of claim 10, wherein each first and second aperture in each of the plurality of sheets has a diameter, the diameter of the first aperture in some the plurality of sheets being different from the diameter of the first aperture in other of the plurality of sheets so that the apparatus has a cross-sectional thickness near the first aperture thereof that is less than a cross-sectional thickness away from the first aperture.

12. The apparatus of claim 11, wherein the diameter of the second aperture in some the plurality of sheets is different from the diameter of the second aperture in other of the plurality of sheets so that the apparatus has a cross-sectional thickness near the second aperture that is less than a cross-sectional thickness away from the second aperture.

13. The apparatus of claim 12, wherein the cross-sectional thickness of the apparatus tapers to a reduced dimension surrounding each of the first and second apertures thereof.

14. The apparatus of claim 13, wherein sheets at axially opposed ends of the apparatus sandwich a plurality of intermediate sheets therebetween, the first and second apertures of the axially opposed sheets having diameters that are at least equal to the corresponding diameters of the first and second apertures of the intermediate sheets.

15. The apparatus of claim 9, further including a third aperture formed through the prosthesis intermediate the first and second apertures, a bridge of the flexible tissue material interconnecting opposed sides of the third aperture.

16. The apparatus of claim 15, further including a recessed portion in a sidewall intermediate the first and second apertures and located opposite the recess.

17. A meniscal prosthesis for replacement of meniscus of a knee joint, comprising:
   a plurality of generally flat sheets of a flexible tissue material, the plurality of sheets being attached together substantially coaxially so as to inhibit movement between adjacent sheets the plurality of sheets, at least one aperture extending substantially coaxially through the plurality of sheets.

18. The prosthesis of claim 17, wherein the at least one aperture further comprises first and second apertures extending axially through the plurality of sheets, the first and second apertures being located relative to each other according to associated apertures of a patient's lateral and medial menisci.

19. The apparatus of claim 6, wherein the central aperture defines an inner diameter for each of the plurality of sheets and an outer diameter is defined by an outer periphery of the plurality of sheets, some of the sheets having different inner diameters so that the apparatus has a cross-sectional thickness near a central aperture thereof that is less than a cross-sectional thickness near the outer periphery thereof.

20. The apparatus of claim 19, wherein the cross-sectional thickness of the apparatus tapers to a reduced dimension near the central aperture thereof.

* * * * *